United States Patent [19]

Bahrmann et al.

[11] Patent Number: 4,710,321
[45] Date of Patent: Dec. 1, 1987

[54] QUATERNARY AMMONIUM SALTS OF SULFONATED TRIARYLPHOSPHINES AND PROCESS FOR THE PRODUCTION THEREOF

[75] Inventors: Helmut Bahrmann, Hamminkein; Boy Cornils, Dinslaken; Wolfgang Lipps, Oberhausen; Peter Lappe, Oberhausen; Helmut Springer, Oberhausen, all of Fed. Rep. of Germany

[73] Assignee: Ruhrchemie Aktiengesellschaft, Fed. Rep. of Germany

[21] Appl. No.: 22,274

[22] Filed: Mar. 5, 1987

Related U.S. Application Data

[62] Division of Ser. No. 738,868, May 29, 1985, Pat. No. 4,673,535.

[30] Foreign Application Priority Data

Jun. 1, 1984 [DE] Fed. Rep. of Germany ....... 3420493

[51] Int. Cl.$^4$ ............................................ C07C 87/30
[52] U.S. Cl. ................................................ 200/501.15
[58] Field of Search .................................... 260/501.15

[56] References Cited

U.S. PATENT DOCUMENTS

| | | | |
|---|---|---|---|
| 1,867,022 | 7/1932 | Munz et al. | 260/501.15 |
| 2,605,281 | 7/1952 | Blinoff | 260/501.15 |
| 3,383,410 | 5/1968 | Johnson et al. | 260/501.15 |
| 3,706,789 | 12/1972 | Bergstrom et al. | 260/501.15 |
| 3,819,656 | 6/1974 | Barie et al. | 260/501.15 |
| 3,992,432 | 11/1976 | Napier et al. | 568/811 |
| 4,248,802 | 2/1981 | Kuntz | 568/909 |
| 4,455,295 | 6/1984 | Hopp et al. | 260/501.15 |

FOREIGN PATENT DOCUMENTS

| | | |
|---|---|---|
| 107006 | 5/1984 | European Pat. Off. . |
| 2627354 | 12/1976 | Fed. Rep. of Germany . |
| 2700904 | 7/1977 | Fed. Rep. of Germany . |
| 2733516 | 2/1978 | Fed. Rep. of Germany . |
| 1066261 | 4/1967 | United Kingdom . |

*Primary Examiner*—J. E. Evans
*Attorney, Agent, or Firm*—Bierman & Muserlian

[57] ABSTRACT

The invention relates to new quaternary ammonium salts of di and trisulfonated triarylphosphines as well as a process for their preparation. The salts are of Formula I

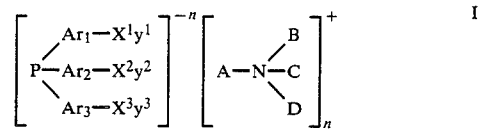

wherein $Ar_1$, $Ar_2$, and $Ar_3$ are each independently an aryl; $X^1$, $X^2$, and $X^3$ are each independently a sulfogroup; $y^1$, $y^2$, and $y^3$ are each independently 0 or 1, provided that their sum is at least 1; A is an alkyl, hydroxyalkyl, aralkyl, or aryl having 6–25 carbon atoms; B, C, and D are straight chain or branched alkyl having 1–4 carbons; and n is a whole number of 1–3.

20 Claims, No Drawings

QUATERNARY AMMONIUM SALTS OF SULFONATED TRIARYLPHOSPHINES AND PROCESS FOR THE PRODUCTION THEREOF

PRIOR APPLICATION

This application is a division of U.S. patent application Ser. No. 738,868 filed May 29, 1985, now U.S. Pat. No. 4,673,535.

This Application claims the priority of German Application P 34 20 493.8, filed June 1, 1984.

The instant invention relates to new quaternary ammonium salts of mono, di, and trisulfonated triarylphosphines. Many sulfonated triarylphosphines and their salts are known in the art. For example, the sodium salt of diphenylphosphine phenyl-m-sulfonic acid is obtained by treating triphenylphosphine with oleum and subsequently neutralizing the reaction mixture with saturated sodium hydroxide solution (Ahrland, Chatt, J. Chem. Soc. 1958, 276). The di and trisulfonated compounds, phenylphosphine di-(m-phenyl)sulfonic acid and triphenylphosphine tri-(m-sulfonic acid) or their salts, can be prepared by varying the reaction conditions, in particular the reaction time and the reaction temperature, as well as the ratio of triphenylphosphine to sulfur trioxide.

The sulfonation process described above is not only suitable for the introduction of $SO_3H$ groups onto the phenyl groups of triphenylphosphine, but it can also be used to sulfonate substituted phenyl groups such as the tolyl, xylyl, chlorophenyl. In addition, condensed aromatic hydrocarbons in triarylphosphines, such as the naphthyl group, can also be sulfonated with his procedure. The potassium salt, alkaline earth salts and other salts can be prepared by neutralizing of the sulfonation mixture with the corresponding metal bases.

The free sulfonic acid is formed by treatment of, for example, the sodium salt with a cation exchanger. Further salts may generally be prepared by neutralizing the free acid with hydroxides or carbonates. Lead, zinc, copper, ammonium, and quaternary ammonium salts [having the general formula $N(R_1R_2R_3R_4)^+$, wherein $R_1$, $R_2$, $R_3$ and $R_4$ are each straight-chained or branched $C_1$–$C_4$ alkyl] can thus be obtained in the form of their aqueous solutions such as solids after evporation under reduced pressure.

Pure salt preparation by a proven process is described in DOS 32 35 030. In this process, the sulfonation product is treated with the solution of a water-insoluble amine in a water-insoluble solvent. This converts the acid into the amine salt, which transfers to the organic phase. This is separated and the sulfonated triarylphosphine, which is now present in the organic phase, is treated with an aqueous base to transfer it into a new aqueous phase. It can then be isolated from the new aqueous phase in purified form.

The salts of sulfonated triarylphosphines find application in various chemical technologies. According to British Pat. No. 1,006,261, they are added to photographic emulsions as anti-fogging agents. In German Pat. No. 27 33 516, a process is described for the telomerization of dienes by the reaction of a diene with a compound having a mobile hydrogen atom in the presence of a catalyst which consists of a transition metal, in particular palladium, or a transition metal compound of Group VIII of the Periodic Table and a water-soluble triarylphosphine having the general formula $P(C_6H_4SO_3M)_n(C_6H_5)_{3-n}$.

According to German Pat. No. 27 00 904, the addition of hydrogen cyanide to organic compounds containing at least one ethylene double bond takes place in the presence of a catalyst system which contains a triphenylsulfonate as well as a nickel, iron or palladium compound. Additionally, these sulfonated compounds find utility as catalysts in the preparation of aldehydes by the addition of carbon monoxide and hydrogen to olefins as described in the German Pat. No. 26 27 354.

Quaternary ammonium salts of the invention find application as components of water-soluble catalyst systems which also contain metals, in particular noble metals, for the reaction of organic compounds in two-phase systems comprising an organic and an aqueous phase. They enhance the solubility of the organic substrate in the aqueous phase and thus contribute to an increase in conversion. Their extremely low solubility in the organic phase means that the metal components of the catalyst are not removed with the organic reacion product from the reaction zone, or if so, only in negligibly small amounts. This property of the new compounds is of particular importance when noble metal catalysts are employed because in many cases a complete, or nearly complete, recovery of the noble metal is the decisive factor between economic feasibility and impracticality of the process.

The present invention is directed to new quaternary ammonium salts of mono, di, and trisulfonated triarylphosphines of the general formula:

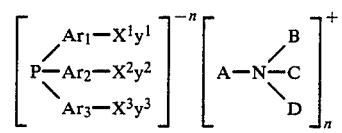

wherein $Ar_1$–$Ar_3$ are each independently an aryl group and $X^1$–$X^3$ are independently a sulfo group, while $y^1$, $y^2$, and $y^3$ are 0 or 1, provided that at least one of $y^1$, $y^2$, or $y^3$ is 1. A is an alkyl, hydroxyalkyl, aralkyl, or aryl group, and has 6 to 25 carbon atoms. B, C and D are straight-chain or branched alkyl groups having 1 to 4 carbon atoms, and n is 1, 2, or 3.

Examples of the Ar group are phenyl, tolyl, xylyl, alkoxyphenyl, and naphthyl group, among others. A is examplified by hexyl, octyl, dodecyl, tetradecyl, hexadecyl, benzyl, phenylethyl, phenyl, tolyl, xylyl, and others. The alkyl groups B, C, and D include methyl, ethyl, propyl, i-propyl, butyl and i-butyl.

The new compounds can be prepared directly from the reaction mixture resulting from the sulfonation of triarylphosphines. To this end, the sulfonation product is mixed at a temperature of about 0° C. to about 90° C., preferably about 20° C. to about 40° C., with enough water to yield a solution containing about 0.5% to about 50% by weight, preferably about 25% to about 30% by weight, sulfuric acid. A water-insoluble amine, dissolved in a water-insoluble organic solvent, is then added to this aqueous solution. The concentration of the amine solution which is added is about 0.5% to about 35% by weight, preferably about 10% to about 30% by weight and more preferably about 15% to about 25% by weight. The amine solution is added in an amount such that about 0.5 mole to about 1.5 mole, preferably about 0.8 mole to about 1.2 mole, is used per equivalent of sulfonic acid. The two liquid phases are intensively mixed, whereby the sulfonated arylphosphine enters the organic phase as the amine salt, while the unreacted sulfuric acid remains in the aqueous phase. The organic phase is then separated.

In order to recover the quaternary ammonium salts, the amine salt dissolved in the organic phase is reacted with an aqueous solution of an equivalent amount of quaternary ammonium hydroxide. An aqueous solution of the quaternary ammonium salt is obtained. The water-insoluble amine is recovered, dissolved in the organic solvent, and can be used again.

The quaternary ammonium hydroxide is advantageously added to the organic phase in fractions until a certain previously determined pH value is reached, and the respective aqueous phases are preferably worked up separately thereafter. However, this is only a preferred embodiment. The entire amount of quaternary ammonium hydroxide may be added at one time.

The amounts of quaternary ammonium hydroxide required for the conversion of the amine salt can either be determined mathematically, allowing for the composition of the amine salt, or by means of preliminary experiments. When preliminary experiments are carried out, correspondingly small changes in the pH value are measured as a function of the ammonium hydroxide consumption, and the aqueous phases which are obtained separately are analysed.

Alternatively, one can remove small amounts of sulfate which may be present by first reacting the organic phase, containing the amine salt, with an aqueous alkali-metal hydroxide solution. In this case, it is also preferable that the solution be added only until a pre-determined pH value is reached. The aqueous phase is separated off and the organic phase is then mixed with the corresponding amount of quaternary ammonium hydroxide. The specific pH to which one will add the solution will be readily determined by known methods and varied by those skilled in the art.

In order to prepare particularly pure compounds, the amine salt dissolved in the organic phase is not converted directly into the quaternary ammonium salt, but first to another salt, e.g. an alkali or alkaline earth salt, by reaction with the corresponding base. The fractional addition of solutions and working up the individual fractions separately is also advantageous in this case. The fractional method allows one to separate the products of various sulfonation steps as well as phosphine oxides and phosphines sulfides in a convenient manner.

The solid salt is recovered by evaporation or crystallization and can be further purified by recrystallization. It is subsequently dissolved in water, converted into the free sulfonic acid by acidification with dilute mineral acid, preferably sulfuric acid, and as described above, extracted as an amine salt and converted to the quaternary ammonium salt.

In the above process for the preparation of the new compounds, water-insoluble amines include amines having carbocyclic and heterocyclic aliphatic, aromatic, araliphatic and especially open-chained, branched or unbranched aliphatic groups having about 10 to about 60, preferably about 13 to about 36, carbon atoms.

Amines whose sulfonated arylphosphine salts are either insoluble or have only limited solubility in the organic solvent are less suitable. Amines which have been successfully employed as the water-insoluble amine include: tri-n-octylamine, tri-iso-octylamine, tri-2-ethylhexylamine, methyl-di-octylamine, and tri-dodecylamine. Aliphatic or aromatic hydrocarbons or hydrocarbon mixtures, e.g. toluene or fractions similar to kerosine are particularly suitable as water-insoluble solvents, as are $C_4$–$C_{20}$ alcohols or $C_8$–$C_{20}$ ethers.

The quaternary ammonium hydroxides are employed as the aqueous solutions formed during their preparation from their corresponding salts by reaction with anion exchangers, or from their halides by reaction with silver hydroxide.

For many applications, the aqueous solutions of the quaternary ammonium salts of the sulfonated triarylphosphines which result from the instant preparation can be used directly. Still, recovery of the salts in crystalline form may be desirable. In order to obtain the crystalline salts, their aqueous solutions are evaporated under reduced pressure at about 10 to about 50 mbar ($1 \times 10^3$ to $5 \times 10^3$ Pa).

The new compounds form colourless crystals which readily dissolve in water. They are also soluble in lower alcohols and difficultly soluble or insoluble in toluene, acetone, tetrahydrofuran, and acetonitrile.

Quaternary ammonium salts with the general formula given above and in which Ar is a phenyl or naphthyl group; the sum of $y^1$, $y^2$, and $y^3$ is 2 or 3; and B, C and D denote the same straight-chained or branched alkyl groups with 1 to 4 carbon atoms have proved to be particularly suitable as components of catalyst systems.

The following examples illustrate, but do not limit the invention. The abbreviations used have the following meanings:
TPPMS: triphenylphosphine monosulfonic acid salt
DS: triphenylphosphine disulfonic acid salt
TS: triphenylphosphine trisulfonic acid salt
OMS: triphenylphosphine oxide monosulfonic acid salt
ODS: triphenylphosphine oxide disulfonic acid salt
OTS: triphenylphosphine oxide trisulfonic acid salt
SDS: triphenylphosphine sulfide disulfonic acid salt
STS: triphenylphosphine sulfide trisulfonic acid salt

EXAMPLE 1

Preparation of TPPDS (sodium salt)

1280 g of 30% oleum (D=1.94) are placed in a 1 liter flask equipped with a stirrer, thermometer, dropping funnel and cooler and cooled under nitrogen to a temperature of 15° C. 105 g (0.4 mole) triphenylphosphine are added, with stirring, over a period of 2 hours. The reaction temperature is maintained between 15° and 20° C. After the triphenylphosphine has been added, the reaction mixture is stirred for another 3.5 hours at 20° C.

The flask contents are then transferred, under a nitrogen atmosphere, to a 6 liter flask containing 2505 g of water at about 10° C. During the transfer, the temperature is maintained between 20° C. and 40° C. by intensive external cooling.

The reaction mixture has the following composition (m=3890 g):

|  | mass (g) | mMole | Mole %[1] |
| --- | --- | --- | --- |
| TPPDS | 117.8 | 253 | 64.6 |
| TS | 30.3 | 53 | 13.5 |
| ODS | 26.0 | 54 | 13.8 |
| OTS | 8.6 | 15 | 3.8 |
| SDS | 8.2 | 17 | 4.3 |

[1]calculated as sodium salts.

The homogeneous sulfonation mixture with the above composition is stirred into a mixture of 303 g (858 mMole) triisooctylamine and 1212 g toluene in a 6 liter flask under a nitrogen atmosphere. After the addition has been completed, the flask contents are stirred for 30 minutes and then left to stand for an additional 30 minute period. The bottom phase (3665 g of aqueous sulfuric acid) is separated off and discarded.

The organic phase (1731 g) has the following composition:

|  | mass (g) | mMole | Mole %[1] |
| --- | --- | --- | --- |
| TPPDS | 116.4 | 250 | 66.8 |
| TS | 29.1 | 51 | 13.6 |
| ODS | 24.2 | 50 | 13.4 |
| OTS | 4.3 | 7 | 1.9 |
| SDS | 7.9 | 16 | 4.3 |

[1]calculated as sodium salts

The extraction product is then mixed with 3% aqueous sodium hydroxide solution under a nitrogen atmosphere in a 4-liter flask, and the pH is measured with a conventional glass electrode. When the desired pH has been reached, sodium hydroxide addition is stopped. The two-phase system which is formed, containing triisooctylamine, toluene and the sodium salt of the sulfonated triphenylphosphines (as well as the corresponding phosphine oxides and phosphine sulfides), is separated. The water-free organic phase is again mixed with an aqueous sodium hydroxide solution and separated; the resulting organic phase is either dispensed with or used again for the extraction of sulfonation mixtures.

The salt solution (848 g), separated off in the pH range of 6.0–6.6 at 22° C., is stirred for about 16 hours under a nitrogen atmosphere until crystallization is completed. This is then mixed with 400 ml of methanol. The crystalline slurry is freed from the mother liquor by filtration with a glass frit, washed with methanol, and dried in a vacuum.

A fine-crystalline white substance with the following composition is obtained:
TPPDS: 90.92%
TS: 0.61%
ODS: 0.83%
SDS: 1.21%
$H_2O$: 5.8%
P(III): 1.97%

EXAMPLE 2

Preparation of TPPTS (sodium salt)

In accordance with Example 1, 1280 g of 30% oleum are placed in a 1 liter flask. 105 g (0.4 mole) of triphenylphosphine are added over a period of 2 hours. The mixture is then stirred for another 24 hours at 20° C. The reaction mixture is then added to 2502 g of water at a temperature of 10° C. 3887 g of a sulfonation mixture with the following composition are obtained:

|  | mass (g) | mMole | Mole %[1] |
| --- | --- | --- | --- |
| TPPDS | 62.2 | 133 | 33.0 |
| TS | 117.6 | 207 | 51.4 |
| ODS | 12.0 | 25 | 6.2 |
| OTS | 17.5 | 30 | 7.4 |
| STS | 4.7 | 8 | 2.0 |

[1]calculated as sodium salts

The homogeneous sulfonation mixture with the above composition is mixed with a mixture of 388 g (1099 mMole) triisooctylamine and 1552 g toluene in accordance with Example 1. After phase separation, 3660 g of an aqueous sulfuric acid solution and 2167 g of organic phase with the following composition are obtained:

|  | mass (g) | mMole | Mole %[1] |
| --- | --- | --- | --- |
| TPPDS | 61.9 | 133 | 34.3 |
| TS | 117.5 | 207 | 53.4 |
| ODS | 11.5 | 24 | 6.2 |
| OTS | 10.2 | 17 | 4.4 |
| STS | 4.4 | 7 | 1.7 |

[1]calculated as sodium salts

The sulfate concentration in the organic phase is 1.44% by weight.

The extraction product is reextracted with a 10% aqueous sodium hydroxide solution in the manner set forth in Example 1.

The salt solution (482 g), separated in the pH range of 5.3 to 5.9 at 24° C., is reduced to 250 g with the aid of a rotary evaporator and then stirred for 12 hours at room temperature. The crystalline slurry is freed from the mother liquor by filtration with a glass frit, washed with methanol, and dried in vacuum.

A white fine-crystalline solid with the following composition is obtained:
TPPDS: 4.20%
TS: 91.40%
ODS: 0.50%
OTS: 0.27%
SDS: 0.06%
STS: 0.73%
$H_2O$: 2.5%
P(III): 1.698 Mole/kg

EXAMPLE 3

Preparation of TPPTS benzyltrimethylammonium salt $P(C_6H_4SO_3)_3[(C_6H_5CH_2)N(CH_3)_3]_3$ 50 g TPPTS sodium salt (prepared in accordance with Example 2) are dissolved in 250 g water with stirring in a 4 liter three-necked flask, under a nitrogen atmosphere. This is mixed with 940 g of a 10% sulfuric acid solution. Then a mixture of 70.6 g (200 mMole) triisooctylamine and 282.4 g toluene is added dropwise. After the mixture is added, the solution is stirred for 15 minutes and left to stand for an additional 15 minutes. The bottom phase (1193 g of aqueous sulfuric acid) is separated off and discarded.

The organic phase (388 g) is mixed, at 26° C., with a 10% sodium hydroxide solution in a 1 liter flask with stirring under a nitrogen atmosphere until a pH of 4.75 is reached. The two-phase system which is formed is separated, and the remaining water-free organic phase is washed twice, each time with 100 g $H_2O$. After phase separation, the organic phase is mixed with 73.3 g of a 40% aqueous solution of benzyltrimethylammonium hydroxide (176 mMole, pH 6.0). The salt solution separated off (107 g) has the following composition:

|  | mass (g) | mMole | Mole %[1] |
| --- | --- | --- | --- |
| TPPDS | 1.9 | 4.1 | 7.6 |
| TS | 27.5 | 48.4 | 89.5 |
| OTS | 0.1 | 0.2 | 0.4 |

|  | mass (g) | mMole | Mole %[1] |
| --- | --- | --- | --- |
| SDS | 0.1 | 0.2 | 0.4 |
| STS | 0.7 | 1.2 | 2.1 |

[1]calculated as sodium salt

The salt solution is concentrated, under a vacuum, with a rotary evaporator. The residue, which is highly viscous, is recrystallized from methanol. A white crystalline solid of the following composition[2] is obtained:
TPPDS: 2.27%
TS: 94.30%
STS: 1.26%
P(III): 1.03 Mol/kg
N: 4.31%
Na: 0.055%
(2) as benzyltrimethylammonium salts

EXAMPLE 4

Preparation of TPPTS phenyltrimethylammonium salt $P(C_6H_4SO_3)_3[H_5C_6N(CH_3)_3]_3$ In accordance with Example 3, 50 g TPPTS Na salt (prepared in Example 2) are dissolved in 250 g water with stirring and mixed with 940 g of a 10% sulfuric acid solution. After the addition of 70.6 g (200 mMole) triisooctylamine and 282.4 g toluene, stirring is continued for another 15 minutes. Phase separation takes place and the remaining organic phase (390 g) is reextracted with a 10% sodium hydroxide solution (as in Example 3) until pH 4.7. The organic phase is subsequently washed twice with water, and finally mixed with 114.4 g of a 25% aqueous phenyltrimethylammonium hydroxide solution (187 mMole, pH: 6.7).

The salt solution which is separated (146 g) has the following composition:

|  | amount (g) | mMole | Mole %[1] |
| --- | --- | --- | --- |
| TPPDS | 2.1 | 4.5 | 7.0 |
| TS | 31.9 | 56.2 | 89.0 |
| OTS | 0.2 | 0.3 | 0.5 |
| SDS | 0.2 | 0.4 | 0.6 |
| STS | 1.5 | 2.5 | 3.9 |

[1]calculated as the sodium salt

The salt solution is freed from the water under vacuum, and the remaining residue is recrystallized from i-propanol/ethyl acetate. A white crystalline solid with the following composition[3] is obtained:
TPPDS: 4.03%
TS: 90.83%
STS: 1.90%
P(III): 1.04 Mole/kg
N: 4.48%
Na: 0.055%
(3) as a phenyltrimethylammonium salt

EXAMPLE 5

Preparation of TPPTS dodecyldiemethylethylammonium salt $P(C_6H_4SO_3)_3[H_{25}C_{12}N(CH_3)_2(C_2H_5)]_3$ In the same manner as in Example 3, 50 g of TPPTS Na salt (prepared in Example 2) are dissolved with stirring in 250 g water. The solution is mixed with 940 g of a 10% sulfuric acid solution. After the addition of 70.6 g (200 mMole) tri-isooctylamine and 282.4 g toluene, stirring is continued for another 15 minutes.

The organic phase remaining after phase separation (387 g) is reextracted with a 10% sodium hydroxide solution until pH 4.7 is reached. Then the organic portion is washed twice, each time with 100 g water, and finally mixed with 231 g of 20% aqueous dodecyldimethylethylammonium hydroxide (178 mMole, pH: 6.3). The salt solution separated off (275 g) has the following composition:

|  | amount (g) | mMole | Mole %[1] |
| --- | --- | --- | --- |
| TPPDS | 1.8 | 3.9 | 7.0 |
| TS | 28.3 | 49.8 | 89.6 |
| SDS | 0.1 | 0.2 | 0.4 |
| STS | 1.0 | 1.7 | 3.0 |

[1]calculated as sodium salts.

The salt solution is placed in a vacuum to remove water therefrom. The remaining highly viscous residue is dried in a vacuum over $P_2O_5$. A white crystalline solid is obtained having the following composition[4]:
TPPDS: 2.95%
TS: 90.35%
STS: 2.71%
P(III): 0.77 Mole/kg
N: 3.33%
Na: 0.055%
(4) as dodecyldimethylethylammonium salt

EXAMPLE 6

Preparation of TPPDS-benzyltrimethylammonium salt $(H_5C_6)P(C_6H_4SO_3)_2[(C_6H_5CH_2)N(CH_3)_3]_2$ 50 g TPPDS Na salt (prepared in Example 1) is added to 250 g water while stirring and mixed with 817 g of 10% sulfuric acid whereupon the solid dissolves. Then a mixture of 60.0 g (170 mMole) triisooctylamine and 240.0 g toluene is added dropwise. After completion of the addition, the solution is stirred for 15 minutes and then left to stand for 15 minutes. The bottom phase (1073 g of aqueous sulfuric acid) is separated off and discarded. The organic phase (338 g) is stirred with 3% sodium hydroxide solution in a 1 liter flask at 23° C. under a nitrogen atmosphere until pH of 4.8 is reached. The two-phase system which is formed is separated; the remaining organic phase is washed twice, each time with 100 g water. After phase separation, the organic phase is mixed with 68.6 g of a 40% aqueous benzyltrimethylammonium hydroxide solution (164 mMole, pH: 6.1). The salt solution which is separated therefrom (108 g) has the following composition:

|  | amount (g) | mMole | Mole %[1] |
| --- | --- | --- | --- |
| TPPDS | 37.5 | 80.5 | 98.3 |
| ODS | 0.3 | 0.6 | 0.7 |
| SDS | 0.4 | 0.8 | 1.0 |

[1]calculated as Na salt

The salt solution is evaporated to dryness in a vacuum. The residue, a white crystalline solid has the following composition[5]:
TPPDS: 93.75%
ODS: 1.19%
SDS: 1.08%
P(III): 1.33 Mole/kg
N: 3.81%

Na: 0.05%
(5) as benzyltrimethylammonium salt

EXAMPLE 7

Preparation of TPPDS-phenyltrimethylammonium salt $(H_5C_6)P(C_6H_4SO_3)_2[(H_5C_6)N(CH_3)_3]_2$ As in Example 6, 50 g of TPPDS Na salt (prepared in Example 1) are mixed with 250 g water and then with 817 g of 10% sulfuric acid under continuous stirring. After the addition of 60.0 g (170 mMole) triisooctylamine and 240.0 g toluene, the mixture is stirred for another 15 minutes.

After phase separation, the remaining organic phase (337 g) is reextracted with 3% sodium hydroxide solution until a pH of 4.7 is reached. Then the remaining organic portion is washed twice, each time with 100 g water, and finally mixed with 98.7 g of a 25% aqueous phenyltrimethylammonium hydroxide solution (161 mMole, pH: 6.2).

The salt solution removed therefrom (138 g) has the following composition:

|  | amount (g) | mMole | Mole %[1] |
|---|---|---|---|
| TPPDS | 37.3 | 80.0 | 98.3 |
| ODS | 0.3 | 0.6 | 0.7 |
| SDS | 0.4 | 0.8 | 1.0 |

[1] calculated as Na salt

The salt solution is evaporated to dryness in a vacuum. The residue, a white crystalline solid, has the following composition[3]:
TPPDS: 96.94%
SDS: 1.18%
P(III): 1.38 Mol/kg
N: 3.99%
Na: 0.04%
(3) as phenyltrimethylammonium salt

EXAMPLE 8

Preparation of TPPDS dodecyldimethylethylammonium salt $(H_5C_6)P(C_6H_4SO_3)_2[(H_{25}C_{12})N(CH_3)_2(C_2H_5)]_2$ In accordance with Example 6, 50 g of TPPDS Na salt (prepared in Example 1) are first mixed with stirring with 250 g H$_2$O and then with 817 g of 10% sulfuric acid. Then 60 g (170 mMol) triisooctylamine and 240.0 g toluene are added, and the mixture is stirred for another 15 minutes. After phase separation, the remaining organic phase (340 g) is reextracted with 3% sodium hydroxide solution, as in Example 6, until a pH of 4.9 is reached. The remaining organic phase is then washed twice, each time with 200 g water, and finally mixed with 200 g of a 20% aqueous dodecyldimethylethylammonium hydroxide solution (154 mMole, pH: 6.5).

The salt solution separated off (280 g) has the following composition:

|  | amount (g) | mMole | Mole %[1] |
|---|---|---|---|
| TPPDS | 35.9 | 77.0 | 97.2 |
| ODS | 0.6 | 1.2 | 1.5 |
| SDS | 0.5 | 1.0 | 1.3 |

[1] calculated as Na salt

The salt solution is evaporated to dryness in a vacuum. The residue, a white solid, as the following composition:
TPPDS: 94.95%[4]
SDS: 1.17%
P(III): 1.04 Mol/kg
N: 3.01%
Na: 0.05%
(4) as dodecyldimethylethylammonium salt

EXAMPLE 9

Preparation of TPPMS benzyltrimethylammonium salt $(H_5C_6)_2P(C_6H_4SO_3)[C_6H_5CH_2N(CH_3)_3]$ In accordance with Example 1, 1,000 g of 25% oleum are placed in a 1 liter flask and cooled to 20° C. Over a period of two hours, 204 g (0.78 mole) triphenylphosphine are added with stirring. Then the mixture is stirred for another 2 hours at 20° C.

The reaction mixture is then added to 3012 g water at 10°–15° C. 4216 g of a sulfonation mixture are obtained with the following composition:

|  | mass (g) | mMole | Mole %[1] |
|---|---|---|---|
| TPP | 81.2 | 310 | 39.6 |
| TPPMS | 140.4 | 386 | 49.4 |
| DS | 25.4 | 55 | 7.0 |
| TS | 0.5 | 1 | 0.1 |
| OMS | 10.1 | 27 | 3.5 |
| ODS | 1.5 | 3 | 0.4 |

[1] sulfonated products calculated as sodium salts

The above homogeneous sulfonation mixture is mixed with a mixture of 552 g (1.56 mole) triisooctylamine and 2208 g toluene. After phase separation, 3895 g of an aqueous sulfuric acid solution and 3079 g of organic phase with the following composition are obtained:

|  | mass (g) | mMole | Mole %[1] |
|---|---|---|---|
| TPP | 80.7 | 308 | 39.6 |
| TPPMS | 140.2 | 385 | 49.5 |
| DS | 25.4 | 55 | 7.1 |
| TS | 0.4 | 1 | 0.1 |
| OMS | 9.7 | 26 | 3.3 |
| ODS | 1.3 | 3 | 0.4 |

[1] sulfonated products calculated as sodium salts.

The sulfate concentration in the organic phase is 3.30% by weight.

In accordance with Example 1 the organic extraction product is successively reextracted, with 8% sodium hydroxide solution until a pH of 6.0 is reached, then with 3% sodium hydroxide solution until a pH of 7.0 is reached, and finally with 118 g of a 40% aqueous benzyltrimethylammonium hydroxide solution (283 mMole). The salt solution which is separated off (221 g) has the following composition:

|  | mass (g) | mMole | Mole %[1] |
|---|---|---|---|
| TPPDS | 0.8 | 1.7 | 0.6 |
| MS | 97.4 | 267.6 | 95.4 |
| OMS | 4.2 | 11.1 | 4.0 |

[1] calculated as Na-salt

The salt solution is concentrated under vacuum with the aid of a rotary evaporator. The solid, which precipitates during cooling, is filtered off, washed with a little cold methanol, and dried in a vacuum.

A white crystalline solid with the following composition is obtained:
TPPPMS: 98%[2]
P(III): 1.97 Mol/kg
N: 2.76%
Na: 0.04%
H$_2$O: 0.27%

[2] as benzyltrimethylammonium salt

EXAMPLE 10

Preparation of TPPMS-phenyltrimethylammonium salt $(H_5C_6)_2P(C_6H_4SO_3)[C_6H_5N(CH_3)_3]$ The organic phase (3,000 g) obtained according to Example 9 with the composition given in Example 9 (before reextraction) is successively reextracted with 8% sodium hydroxide solution until a pH of 6.0 is reached, then with 3% sodium hydroxide solution until a pH of 7.0 is achieved, and finally with 171.0 g of a 25% aqueous phenyltrimethylammonium hydroxide solution (279 mMole). The salt solution separated therefrom (273 g) has the following composition:

|       | mass (g) | mMole | Mole %[1] |
|-------|----------|-------|-----------|
| TPPDS | 0.7      | 1.3   | 0.5       |
| MS    | 95.6     | 262.6 | 95.4      |
| OMS   | 4.3      | 11.3  | 4.1       |

[1] calculated as Na salt

The solid, which crystallizes out when the mixture is left to stand at room temperature, is filtered off, washed with a little cold methanol, and dried in a vacuum. A white crystalline solid with the following composition is obtained:
TPPMS: 98%[3]
P(III): 2.04 Mol/kg
N: 2.83%
Na: 0.003%
H$_2$O: 1.81%

[3] as phenyltrimethylammonium salt

What we claim is:

1. A process for the preparation of a quaternary ammonium salt of a mono, di, or trisulfonated triarylphosphine, said salt being of formula I

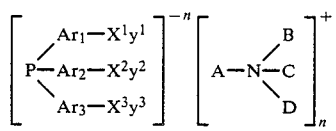

wherein Ar$_1$–Ar$_3$ are each phenyl; X$^1$–X$^3$ are each independently a sulfo group; y$^1$–y$^3$ are each independently 0 or 1, provided that the sum of said y$^1$, y$^2$ and y$^3$ is at least 1; A is benzyl or alkyl of 12 to 18 carbon atoms; B, C and D are each independently straight chain or branched alkyl having 1–4 carbon atoms, and n is 1, 2 or 3, said process comprising (c) sulfonating a triarylphosphine of formula II

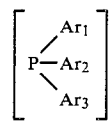

wherein Ar$_1$–Ar$_3$ are each independently phenyl with oleum to form a first reaction product;
(d) mixing said first reaction product with water to form an aqueous mixture;
(e) adding a solution of a water insoluble amine to said aqueous mixture, resulting in a first aqueous phase and a first organic phase;
(f) intensively mixing said aqueous and organic phases;
(g) partitioning the result in step f into a second aqueous phase and a second organic phase;
(h) separating said second organic phase and said second aqueous phase from one another; and
(i) mixing said second organic phase with an aqueous solution of a quaternary ammonium hydroxide of formula III

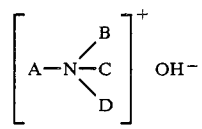

wherein A, and B, C and D have the above definitions
to result in said salt of said formula I.

2. The process of claim 1 wherein, as a result of said mixing in step (i), a third organic phase and a third aqueous phase are produced; said method further comprising
(j) removing said third aqueous phase, containing said salt of Formula I, from said third organic phase.

3. The process of claim 2 further comprising recovering said salt from said said third aqueous phase by vacuum evaporation.

4. The process of claim 1 wherein said water-insoluble amine is cleaned in a water-insoluble solvent prior to said step (e).

5. The process of claim 1 wherein step (d) is carried out at about 0° C. to about 80° C.

6. The process of claim 5 wherein step (d) is carried out at about 20° C. to about 40° C.

7. The process of claim 1 wherein sufficient water is mixed with said first reaction product to result in a sulfuric acid concentration in said aqueous mixture of about 0.5% to about 50% by weight.

8. The process of claim 7 wherein said sulfuric acid concentration in said aqueous mixture is from about 25% to about 35% by weight.

9. The process of claim 1 wherein said water-insoluble amine solution added in step (e) contains said water insoluble amine in a concentration of about 0.5 to about 35% by weight.

10. The process of claim 9 wherein said water insoluble amine solution added in step (e) contains said water insoluble amine in a concentration of about 10% to about 30% by weight.

11. The process of claim 10 wherein said water insoluble amine solution added in step (e) contains said water insoluble amine in a concentration of about 15% to about 25% by weight.

12. The process of claim 1 wherein said water insoluble amine is present during said step (f) in an amount of about 0.5 moles to about 1.5 moles per equivalent of sulfonic acid group.

13. The process of claim 12 wherein said water insoluble amine is present during step (f) in an amount of about 0.8 moles to about 1.2 moles per equivalent of sulfonic acid group.

14. The process of claim 1 wherein said water insoluble amine is of Formula IV

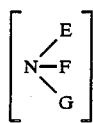
IV wherein E, F and G are each independently,
(1) open, branched or straight, chain aliphatic amines or
(2) homo or heterocyclic aliphatic, aromatic, or araliphatic amines;
said water insoluble amine having about 10–about 60 carbon atoms.

15. The process of claim 14 wherein said water insoluble amine has about 13 to about 36 carbon atoms.

16. The process of claim 14 wherein said E, F, G are all the same.

17. The process of claim 3 wherein said vacumn evaporation is conducted at a pressure of about 10 mbar to about 50 mbar.

18. The process of claim 1 wherein step (i), is replaced with
(k) mixing said second organic phase with an alkali or alkaline earth metal base to form metal salt of said sulfonated triarylphosphine,
(l) separating said metal salt from the remainder of said second organic phase;
(m) acidifying said separated metal salt to yield a free triarylphosphine sulfonic acid;
(n) extracting said free sulfonic acid into a further organic phase containing a water insoluble amine as in steps (d)–(f);
(o) partitioning and separating the resultant mixture to obtain an additional organic phase; and then
(p) carrying out step (i) with said additional organic phase in place of said second organic phase.

19. The process of claim 18 wherein said alkali or alkaline earth metal base is added in portions in step k, and after each addition, step (l) is carried out, the individual fractions being separately processed thereafter.

20. The process of claim 1 wherein said hydroxide of Formula III is added in portions, after each addition, a portion of said salt of Formula I being removed from the remainder of the mixture obtained in step (i).

* * * * *